(12) United States Patent
Maier (10) Patent No.: US 8,592,759 B2
(45) Date of Patent: Nov. 26, 2013

(54) SAMPLE PREPARATION FOR IONIZATION WITH MATRIX-ASSISTED LASER DESORPTION

(75) Inventor: Thomas Maier, Lilienthal (DE)

(73) Assignee: Bruker Daltonik GmbH, Bremen (DE)

( * ) Notice: Subject to any disclaimer, the term of this patent is extended or adjusted under 35 U.S.C. 154(b) by 19 days.

(21) Appl. No.: 13/315,603

(22) Filed: Dec. 9, 2011

(65) Prior Publication Data
US 2012/0152041 A1   Jun. 21, 2012

(30) Foreign Application Priority Data

Dec. 15, 2010  (DE) .................... 10 2010 054 581

(51) Int. Cl.
*H01J 49/26* (2006.01)

(52) U.S. Cl.
USPC ............................ 250/288; 250/281; 250/282

(58) Field of Classification Search
USPC ......................................... 250/281, 282, 288
See application file for complete search history.

(56) References Cited

U.S. PATENT DOCUMENTS

| | | | |
|---|---|---|---|
| 5,705,813 A | 1/1998 | Apffel | |
| 6,287,872 B1 | 9/2001 | Schurenberg | |
| 6,777,245 B2 | 8/2004 | Wixforth | |
| 6,969,166 B2 | 11/2005 | Clark | |
| 2005/0019224 A1 | 1/2005 | Pechter | |
| 2005/0181510 A1 | 8/2005 | Schermer | |
| 2005/0279925 A1* | 12/2005 | Andersson et al. | 250/282 |
| 2009/0221093 A1 | 9/2009 | Reihs | |
| 2011/0084203 A1* | 4/2011 | Basile et al. | 250/282 |

FOREIGN PATENT DOCUMENTS

| | | |
|---|---|---|
| DE | 19949735 A1 | 5/2001 |
| DE | 10164358 A1 | 7/2003 |
| GB | 2341924 A1 | 3/2000 |
| WO | 03015912 A2 | 2/2003 |

OTHER PUBLICATIONS

Karas, M., Bahr, U., Ingendoh, A., Nordhoff, E., Stahl, B. Strupat, K. and Hillenkamp, F., Principles and Applications of Matrix-assisted UV-laser Desorption/Ionization Mass Spectrometry, Analytica Chimica Acta, v. 241, pp. 175-185 (1990).

* cited by examiner

*Primary Examiner* — Nicole Ippolito
(74) *Attorney, Agent, or Firm* — Robic, LLP (57) ABSTRACT

A simplified sample preparation on a sample support for ionization with laser desorption (MALDI or LDCI, for example) includes depositing an analyte material onto a deposition site, providing a sample site which is intended as the substrate for a matrix crystal layer at a distance from the deposition site, and establishing a liquid communication between the deposition site and the sample site. A device for the preparation of samples for ionization with matrix-assisted laser desorption, and a sample support for use with the inventive method are also disclosed.

13 Claims, 4 Drawing Sheets

SAMPLE PREPARATION FOR IONIZATION WITH MATRIX-ASSISTED LASER DESORPTION

PRIOR APPLICATIONS

This patent application claims priority from German patent application 10 2010 054 581.3 filed Dec. 15, 2010, which is hereby incorporated by reference.

BACKGROUND

This invention relates to a method and a device for the preparation of samples for ionization with matrix-assisted laser desorption. MALDI time-of-flight mass spectrometry is often used in clinical microbiology for the identification of microorganisms, particularly those that cause human infectious diseases. The principle of matrix-assisted laser desorption and ionization (MALDI) has already been described in detail elsewhere (see for example M. Karas et al. "Principles and applications of matrix-assisted UV-laser desorption/ionization mass spectrometry", 1990, Analytica Chimica Acta, 241, 175-185). To explain it very briefly: in a widely used version of MALDI sample preparation, soluble analyte molecules are inserted into a structure of matrix crystals which have a high absorptivity for laser light. If the matrix crystal structure is exposed to pulses of laser radiation, it vaporizes explosively and releases the embedded analyte molecules. Analyte molecules are also ionized during this very energetic ablation process. These molecules are therefore available for a subsequent mass spectrometric analysis. For this analysis, the analyte ions are usually accelerated in electric fields to different velocities depending on their masses m and number z of charges, and after they have passed through a long flight path, which resolves them by their velocities, they are fed to a detector with a secondary electron multiplier. The timespans from the laser desorption of the sample material, or from an acceleration pulse in an orthogonal time-of-flight mass spectrometer, until the different ion current signals arrive at the detector give, via a time-to-mass transformation, the mass-to-charge ratios m/z of the analyte ions.

In clinical microbiology, microorganisms of clinical samples, such as mucosal smears, are cultured specifically in order to provide the minimum number of microorganisms which are required for the detection limit of the particular detection method, and to be able to repeat sample-consuming investigations, where necessary. To this end, the clinical sample is often applied to a nutrient medium such as agar. Under suitable culturing conditions, for example at controlled temperature and humidity, distinguishable colonies of the microorganisms are grown on the culture medium.

The usual method of MALDI sample preparation is to manually take up biological material of a single colony on a nutrient medium with an inoculation swab and transfer it to a sample site of a sample support as the analyte material. The biological material thus applied is subsequently wetted with a matrix solution. The matrix solution contains dissolved molecules of the matrix substance, which, as the drying process proceeds, form the crystals into which the analyte molecules are embedded. The matrix solution also contains a solvent which destroys the biological structure of the microorganism, particularly the cell wall. The decomposition process causes soluble material of the microorganism such as proteins or peptides to be released and brought into solution; these are the analyte molecules of actual interest and they are detected in the mass spectrometric analysis. Apart from these analyte molecules, cell residues also remain after decomposition. They are insoluble and thus impede the crystallization of the matrix material.

Owing to these omnipresent cell residues, the quantity of biological material which is transferred with the inoculation swab onto the sample site must be very small and within very narrow quantity tolerances for a mass spectrometric analysis. An optimum quantity is between around 10,000 and 100,000 cells, which usually occupy around one thousandth of a cubic millimeter. Such a quantity is very difficult to see with the naked eye. The insoluble cell residues which remain after cell decomposition as a type of fibrous pulp can impede the formation of a homogeneous crystal structure of the matrix material, especially one which is free from defects. But the matrix crystal structure must have a certain quality, especially in order to ensure that it has the desired absorption characteristics for laser light of a certain wavelength. Otherwise the ionization yield from the laser desorption is too low for informative time-of-flight mass spectra. In practice, the only solution up to now has been to ensure that a suitable quantity is smeared onto the sample site when depositing the biological material by hand. This demands a great deal of skill of the technician preparing the sample, who has to judge the quantity of biological material by eye in order to ensure that, on the one hand, the prepared sample is sufficiently abundant in terms of analyte molecules yet, on the other hand, is not impeded by too large an amount of unsuitable cell residues after the decomposition. It usually takes a long time for a technician to learn to assess how much biological material is suitable for MALDI sample preparation.

The problem of the remaining insoluble cell components which impede the formation of matrix crystals could be avoided if the decomposed cell material is filtered or centrifuged. Particularly when microorganisms are cultured in a liquid nutrient medium such as a blood or broth culture, filtration or centrifugation is performed several times in order to separate out insoluble cell residues, among other things. In contrast to a flat culture medium with colonies which can be spatially restricted, the growing microorganisms in the liquid nutrient medium are spatially dispersed. As a rule, after the growth phase of the microorganisms, the original components of the liquid nutrient medium, for example red blood cells, are selectively decomposed and then separated from the still largely intact cells of the microorganism with the aid of a first filtration or centrifugation. The microorganisms are subsequently destroyed in an extraction agent or solvent. With a further filtration or centrifugation, the insoluble cell components or cell residues of the microorganisms are then removed so that only the soluble cell components which were released by the destruction remain and are available for the sample preparation. This method of sample preparation is very time-consuming, however.

A further problem arises if the biological material to be analyzed requires a long decomposition time. Yeasts are an example of this. In this case, the extraction agent must act on the microorganism over a long period in order to not only destroy the substructure of the outer, resistant cell membranes but also to release the substructures of the cell interior which are actually of interest. If biological material is deposited onto a sample site of a sample support and then wetted with a matrix solution which is intended to effect the decomposition of the cells contained in the biological material, the time available for the matrix solution to act on the cells is limited by the vaporization of the solvent. When the solvent of the matrix solution has evaporated, the decomposition process ends, possibly before the interior of the cell could be extracted. In principle, the matrix solution with which the biological material is wetted could be dosed in a way which ensures the cells are completely decomposed before drying. However, the amounts of matrix solution required for this are found to be too great to be deposited on sample sites which usually cover an area of a few square millimeters. Increasing the area of the sample site whilst maintaining the current preparation practice would mean that a very small, possibly hardly perceptible, quantity of biological material would have to be smeared onto a disproportionately large area in comparison, which makes the positioning of the biological material more difficult, particularly if deposited manually.

In principle, where the biological material is highly resistant against decomposition, this can be countered with correspondingly more concentrated solvents, e.g. strong acids. However, strong solvents usually also impede the formation of a homogeneous matrix crystal structure, which is required for a high-yield desorption process. In order to avoid this problem, the decomposition can be carried out in two steps. In a first step, a strong extraction agent is added to the sample of biological material on the sample site; this completely decomposes the cell structure and is subsequently removed by evaporation. The soluble analyte molecules can then be dissolved again out of the remaining crust of insoluble and soluble cell components on the sample site by adding the conventional matrix solution, which does not decompose so strongly, and are embedded into the matrix which is forming on the sample site. Such a two-step preparation is a lengthy procedure, however, and again has the disadvantage that the insoluble cell components hinder the formation of a homogeneous layer of matrix crystals on the sample site, where both the decomposition and the matrix crystallization take place.

In view of the above, there is a need for a simplified sample preparation on a sample support for ionization with matrix-assisted laser desorption with which the problems with the matrix crystallization described above can be avoided.

SUMMARY

The following summary is included in order to provide a basic understanding of some aspects and features of the disclosure. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

In accordance with the principles of the invention, a method for the preparation of samples for ionization with matrix-assisted laser desorption includes depositing an analyte material onto a deposition site; providing a sample site which is separate (or spaced apart) from the deposition site as the substrate for a matrix-analyte preparation, and generating a liquid communication between the deposition site and the sample site. By means of the liquid communication, a transfer of soluble analyte molecules of interest from the deposition site to the sample site is facilitated while generally impeding the insoluble components from being transferred from the deposition site to the sample site. After a predetermined time period the liquid communication is discontinued.

The liquid communication between a deposition site and a sample site enables the analyte molecules of interest to be separated from the insoluble cell residues at the deposition site, then transferred to the sample site, where the crystallization of the matrix material, with the associated embedding of the analyte molecules into the matrix crystal structure, is not impeded, at least not by the insoluble cell residues, and can therefore proceed more homogeneously. The separation between the deposition site and the sample site is particularly selected such that insoluble cell components of the analyte material on the deposition site cannot influence, negatively affect or impede the matrix crystallization at the sample site. One layer or several layers of crystallized matrix material—possibly with embedded molecules—are referred to simply as a matrix below. The general idea consists in the spatial separation of the provision of an analyte material—decomposed or yet to be decomposed—on the one hand, and the embedding of the soluble analyte molecules resulting from the decomposition into the matrix crystal structure, on the other hand. The soluble analyte molecules are extracted from the decomposed analyte material and diffuse, via the liquid communication, to the actual sample site for laser desorption, or may be conveyed to it by a spreading liquid which contains the analyte molecules.

Liquid communication as defined in this invention can be any type of liquid connection which allows dissolved cell components, such as analyte molecules of interest and other soluble molecules, to be transferred through the volume of liquid of the liquid connection. The transfer takes place, for example, by diffusion due to the concentration gradient in the communicating volumes of liquid, or by the flow of a liquid containing the dissolved analyte molecules from one site to the other. On the sample site, the volume of liquid of the liquid connection can communicate with the volume of liquid of a matrix solution which was deposited on the sample site before or after the liquid communication was established. Additionally, or alternatively, it can communicate on the deposition site with the volume of liquid of an extraction agent which decomposes or has decomposed the cell structures.

It is to be noted here that no additional driving forces have to be exerted on the solved analyte molecules of interest for transferring them from the deposition site to the sample site. It is known, for example, to separate different solved substances by means of electro-osmotic forces which are brought about, in a capillary electrophoresis process, by the application of voltages to a separation medium, such as gel or sometimes also a liquid. Using electric separation fields, however, requires the solved substances of interest to be present in ionized form. By contrast, the present invention does not rely on any such means but rather exploits the ever-present molecular processes in liquids, such as diffusion. It is also to be mentioned that, according to the present invention, the analyte molecules of interest do not have to be present as ions in the solution.

Samples prepared by the method according to the invention have a very uniform matrix elevation across the sample support with only slight height differences. This means that the cloud of analyte molecules released during the laser desorption is smaller than is the case with a matrix with greater height differences. Energy can thus be transferred uniformly and reproducibly to the ions in the acceleration region in the mass spectrometer.

It has been found that the number of soluble analyte molecules which are transferred via the liquid communication from the deposition site to the sample site is sufficient for an ion current signal in the mass spectrometric detector which is sufficiently distinct from the background. This result holds to a large extent regardless of the quantity of biological material—decomposed or yet to be decomposed—so it can be deposited in a widely liberal quantity on the deposition site. The method also allows the number of analyte molecules for each prepared sample to be increased because significantly larger quantities of analyte molecules can be generated for a sample than with preparation methods used so far. The analyte ion concentration required to exceed the detection limit is thus easier to reach. Moreover, the liquid communication can achieve almost equal distribution of the dissolved cell components in the volumes of liquid, for example, the liquid communication and the matrix solution on the sample site, so the analyte molecules are distributed largely uniformly in the matrix after the crystallization. This leveling effect means that analyte molecule concentrations hardly differ at all in the matrix, which simplifies the search for the target region when aligning the desorption laser onto sample sites which have been prepared in this way.

This particularly facilitates the manual sample preparation of biological material as the analyte on a sample support, because the technician performing the preparation can deposit a larger amount of the biological material on the deposition site without having to worry that this will have a negative effect on the crystallization of the matrix material. The method is also suitable for automating the sample preparation because depositing the quantity of analyte material no longer requires great precision, and the demands placed on appropriate spotting robots, which smear biological material onto a deposition site, controlled by a computer program, for example, can be reduced.

Especially when the analyte molecules are distributed according to a concentration gradient, the liquid communication is preferably maintained as long as is necessary in order to ensure that the concentration of soluble analyte molecules in the communicating volumes of liquids is completely equalized between the deposition site and the sample site. The timespan required for this can be empirically determined, and usually depends on the quantity of matrix solution deposited on the sample site and the quantity of liquid producing the liquid communication, for example the flow cross-section formed in it. It is advantageous to keep the volume of liquid involved in the liquid communication small compared to the liquid volumes of an extraction agent on the deposition site and/or the solvent on the sample site in order to ensure that there is no diffusive or convective transfer of insoluble analyte material components, such as individual fiber strands, from the deposition site to the sample site.

In the introduction, MALDI is named as the preferred type of ionization, where ions are created in the desorption cloud generated by a pulsed laser beam. However, it is obvious that in the present invention laser desorption is only important to transfer the analyte molecules into the gaseous phase. The preparation method therefore does not only serve to provide MALDI samples. Rather, the type of ionization can be freely selected as required to suit the application. Laser desorption can be combined with chemical ionization (LDCI), for example, but other types of ionization can also be used. The term ionization with matrix-assisted laser desorption must be understood in a correspondingly broad sense.

The analyte material on the deposition site can be wetted with an extraction agent before the liquid communication is established, thereby bringing about at least partial decomposition of the analyte material. This can be a bio-chemical disintegration. Osmotic forces, for example, can cause a solvent with reduced salt content to penetrate into the interior of the cells of the biological material to be disintegrated, which has a higher salt concentration. In this case, the cell walls cannot withstand the resulting pressure and burst. A further version of biochemical disintegration is decomposition of the cell membrane by the action of enzymes or acids.

To establish the liquid communication, a liquid bridge between the deposition site and the sample site can be produced from the matrix solution, the extraction agent or a combination of both. This simple way of establishing a liquid communication utilizes the solvents or extraction agents already being used, and there is therefore no need for special consideration of whether the liquids to be used are mutually compatible. It is obvious that the extraction agent and the matrix solution can have the same solvents. In this way it is not necessary to provide several solvents or extraction agents to carry out the method. The extraction agent and the matrix solvent can also be different, however.

In an embodiment which serves as an example, the ratio of the quantity of analyte material to the quantity and/or strength of the extraction agent with which the analyte material is wetted is such that the analyte material is almost completely decomposed. In the case of an acid, for example, the acidity is a suitable criterion for the strength of the extraction agent. It is thus also possible to analyze analyte materials, such as yeasts, which have a very resistant cell wall and whose decomposition is therefore difficult—a long decomposition time may be required, for example—in order to identify the components of the cell's interior. By separating the deposition of the analyte material from the embedding of the analyte molecules into a matrix crystal structure, it is possible to allow the decomposition process sufficient time to release the soluble analyte molecules such as proteins or peptides without interfering with the matrix crystallization process.

The liquid communication can be stopped after a predetermined period of time by drying the matrix solution, the extraction agent or both. When the liquid communication is terminated, the diffusion of analyte molecules along a concentration gradient in the direction of the sample site stops. It is preferable if the drying time is sufficient to allow the concentration of analyte molecules to equalize completely, which means an approximately equal distribution of the analyte molecules in the different communicating volumes of liquid. This timespan can be determined empirically. Alternatively, it can be estimated according to Fick's rule, taking into account the volume of liquid deposited and the differences in concentration.

The drying can be controlled, in particular, by heating the region of the sample site (heating being one example of an energy transfer that can be brought about by, for instance, exposing the site to heat radiation, to a flow of hot drying gas or the like), by changing the vapor pressure conditions above the sample site (such as by ventilating), or a combination of both. The volatile components of the liquids can be vaporized faster by applying heat, for example. To this end it is possible to place heating elements or an infrared light source at the sample site and/or at the deposition site. In one version, it is conceivable to continuously exchange the atmosphere above the sample site, in particular by extracting it with the aid of an extraction device, such as a fan or pump, at the sample site and/or deposition site in order to increase the vaporization rate and thus accelerate the drying process.

In a further embodiment, the deposition site and the sample site can be provided on different support structures. This spatial separation provides a more flexible way of depositing an analyte material and embedding the soluble analyte molecules extracted by decomposition into a matrix crystal structure.

The liquid communication can be established and stopped by moving the two carrier structures relative to each other. The relative movement can, for example, consist of a linear movement of the two support structures toward each other, with the fronts of the two support structures facing each other.

The analyte material can contain either microorganisms in untreated form—for example biological material which is taken from a colony on a nutrient medium—or lysed microorganisms. It is not mandatory for the biological material to be decomposed on the deposition site. On the contrary, this can occur beforehand. The advantages of the invention come into play especially if the analyte material deposited on the deposition site still contains such a quantity of soluble and/or insoluble uninteresting cell residues that a homogeneous crystallization of the matrix material could be impeded.

According to a preferred embodiment, the analyte material can be deposited on the deposition site in a solution containing a matrix substance. With this embodiment, it is possible to deposit all the liquids to be used in the method on the sample support in one step, which simplifies the method.

The invention also refers to a method for the preparation of samples for ionization with matrix-assisted laser desorption on a sample support, with which the problems stated in the introduction can be overcome, where an analyte material in the form of microorganisms is deposited in untreated form—for example cells grown in or on a nutrient medium, such as those from a colony on an agar plate—on a deposition site on the sample support; the analyte material is wetted with an extraction agent or solvent, which brings about at least partial decomposition: and at least a portion of the liquid supernatant of the extraction agent or solvent is transferred from the deposition site to a sample site which is a distance away from the deposition site on the sample support. The transfer can be carried out with a pipette, for example, which takes up at least a portion of the liquid supernatant of the extraction agent or solvent which is on the deposition site. The pipette is then moved to the sample site located on the same sample support where it again releases the quantity of extraction agent or solvent taken up, in which some of the analyte molecules extracted from the analyte material by the decomposition are in solution. In one preferred version, a matrix material can already be dissolved in the extraction agent or solvent.

The invention additionally comprises a device for preparing samples for ionization with matrix-assisted laser desorption which can be used to overcome the problems mentioned in the introduction. The device includes a deposition unit with a first holder for a support structure. Furthermore, it has a sample unit which has a second holder for a sample support for ionization with matrix-assisted laser desorption. A positioning device is designed to at least move the first holder and the second holder relative to each other. In addition, the device includes a control system, which is designed to control the operation of the positioning device.

The mode of operation of the positioning device can involve bringing together the first holder and the second holder at least to within a contact distance in response to a control signal from the control system, whereby the front of a support structure located in the first holder and the front of a sample support for ionization with matrix-assisted laser desorption located in the second holder are brought together so that their fronts are facing each other. It is not absolutely necessary to bring about a direct contact between the fronts of the support structure and the sample support, as is explained further below in relation to the example embodiments. The crucial thing is that the positioning device is designed to bring the two holders together so that their two fronts would come into contact if the positioning movement were continued. The contact distance is especially defined via the possibility of establishing a liquid communication.

The deposition unit is preferably provided with a first pipetting device for the automated deposition of liquid onto a support structure located in the first holder. Additionally or alternatively, the sample unit can be equipped with a second pipetting device for the automated deposition of liquid onto a sample support for ionization with matrix-assisted laser desorption located in the second holder. The control system is then especially designed to control the operation of the first pipetting device and/or the second pipetting device.

The first pipetting device and the second pipetting device can be designed for the simultaneous multiple deposition of liquid. This design can accelerate the preparation procedure.

A further embodiment of the device contains sensors which preferably communicate with the control system in order to monitor the liquid communication or the separation between a support structure located in the first holder and a sample support located in the second holder. The plural "sensors" is used here only for linguistic simplicity. The device can also be equipped with just a single sensor. The control system can utilize the measurement data from the sensor or sensors to control the positioning of the holder of the deposition unit and the holder of the sample unit relative to each other. Examples of suitable sensors include proximity sensors, such as ultrasonic sensors or optical sensors working with infrared light, for example.

The invention also relates to a sample support for the deposition of prepared samples for ionization with matrix-assisted laser desorption which has hydrophilic regions surrounded by hydrophobic regions on the surface and which can be used to overcome the problems mentioned in the introduction. Sample supports of this type have been disclosed in the patent specification DE 197 54 978 C1 (or the equivalent GB 2 332 273; U.S. Pat. No. 6,287,872), for example. In practice, the analyte material is deposited on small hydrophilic anchor zones in a hydrophobic environment. In particular, pipetted droplets with dissolved matrix substance and dissolved analyte molecules attach themselves to these anchor zones and crystallize there more uniformly than they would without anchors. In these hydrophilic anchor zones, the crystal conglomerates bind quite tightly to the surface of the sample support. With careful preparation, a reproducibly uniform sensitivity can be achieved.

In accordance with the invention, the known sample supports are developed further so that at least a first hydrophilic region is connected with at least one further hydrophilic region via a hydrophilic bridge on the surface of the sample support. With this design, a liquid communication between a deposition site and a sample site which both take the form of hydrophilic regions is particularly easy to establish because it is supported by the hydrophilic properties of the bridge. The hydrophilic properties cause liquid which is deposited on one of the sites to flow toward the region of the bridge on the surface of the sample support and thus maintain the liquid communication even over a prolonged period.

The hydrophilic regions preferably have diameters of between 100 micrometers and several millimeters. The hydrophilic bridge, in contrast, can take the form of a narrow hydrophilic band between the deposition site and the sample site on the surface of the sample support.

The term "hydrophobic" surface is used here to mean a surface which is not easily wetted by a solvent and is solvent-repellent, even if it should (exceptionally) not be an aqueous solvent. In the case of an oil-based solvent, it should therefore correspondingly be a lipophobic surface. Analyte molecules usually have the best solubility in water, however, sometimes with the addition of organic, water-soluble solvents. Correspondingly, a "hydrophilic" surface is deemed to be a surface which is easily wetted by the type of solvent or extraction agent used, even if it is not an aqueous solution.

It is preferable for the first hydrophilic region to be connected with several further hydrophilic regions via a hydrophilic bridge in each case. A star-shaped arrangement can be selected for this purpose. A hydrophilic region can thus act as a deposition site from which the dissolved analyte molecules can be transferred via hydrophilic bridges to several sample sites by means of liquid communication. This can be useful if a sample of microbial origin is to be analyzed under different laser desorption conditions such as varying fluence, irradiation duration or laser power.

In a further preferred design, the hydrophilic regions can be split up into deposition sites and sample sites, where the deposition sites occupy a larger area on the surface of the sample support than the sample sites, and each deposition site is connected with at least one sample site via a hydrophilic bridge in each case. The larger area occupied by the deposition sites means a larger amount of extraction agent can be used, and hence a more complete decomposition can be achieved for the fundamentally decomposition-resistant analyte materials, such as yeast cells, which are deposited on these deposition sites. Moreover, the deposition site and the sample site on the sample support surface can differ from each other by their different surface properties. A deposition site with a rough surface provides a better adhesion substrate for insoluble cell components, for example, and can thus hinder the formation and distribution of at least individual suspended particles (such as individual fiber strands) in the liquid communicating volumes.

BRIEF DESCRIPTION OF THE DRAWINGS

The invention can be better understood by referring to the following figures. The components in the figures are not necessarily to scale, emphasis instead being placed upon illustrating the principles of the invention (often schematically). In the figures, like reference numerals designate corresponding parts throughout the different views. The drawing shows in.

DETAILED DESCRIPTION

Figure 1:
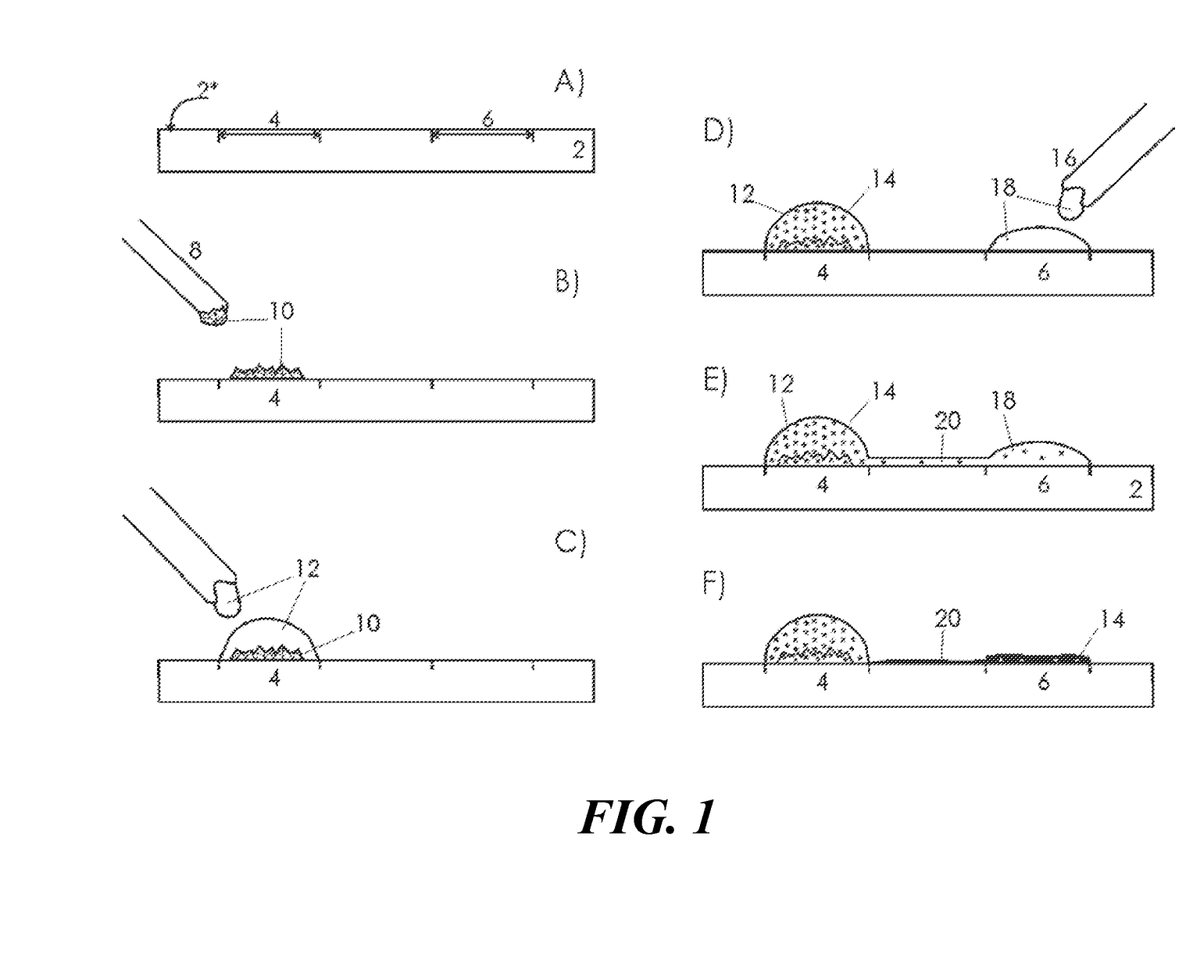
FIG. 1 an example embodiment of a method for sample preparation according to the invention, FIG. 2 a further example embodiment of a method for sample preparation according to the invention, FIG. 3 an example embodiment of a further method for sample preparation according to the invention, FIG. 4A an example embodiment of a device for sample preparation according to the invention shown in an initial preparation configuration, FIG. 4B an example embodiment of the device shown in FIG. 4A moved into a configuration for transferring material from deposition sites to sample sites, FIG. 5 a flow chart of an example procedure, and FIG. 6 an example embodiment of a sample support according to the invention.

FIG. 1 shows an example embodiment of a procedure for sample preparation for ionization with matrix-assisted laser desorption. In FIG. 1A, the first step is to provide a sample support 2, which in this simplified representation has one deposition site 4 and one sample site 6 (the double-headed arrow indicates the dimension). The deposition site 4 and the sample site 6 are arranged at a distance from each other in different regions on the front 2* of the sample support. The separation between the deposition site 4 and the sample site 6 is preferably approximately the same as the separation between two sample sites on conventional MALDI sample supports, in particular a few millimeters. This separation has the advantageous consequence that insoluble cell components of a decomposed analyte material on the deposition site 4 cannot impede the matrix crystallization on the sample site 6. The deposition site 4 and the sample site 6 can differ not only in their spatial separation but also in the fact that they occupy areas of different size and/or different surface properties on the surface of sample support 2.

In FIG. 1B, biological material as the analyte material 10 is deposited on the deposition site 4 using an inoculation swab 8. It can, for example, be smeared on manually by a suitable movement of the inoculation swab 8. Unlike current practice, where crystallization is impeded if a certain quantity of biological material, which may be hardly visible to the human eye, is exceeded, the method according to the invention does not require that a certain dosage of the analyte material 10 be adhered to. It can be applied in very large quantities, for example, in which case the large number of analyte molecules, and thus analyte ions, made available makes it easier to exceed the detection limit in the subsequent mass spectrometric analysis. Manual deposition of the biological material is particularly facilitated in this way.

In FIG. 1C, an extraction agent 12, which brings about the decomposition of the analyte material 10, is deposited on the analyte material 10 on the deposition site 4. The substructure of the cells of the biological material is released in the form of analyte molecules 14 (stars) here, and these molecules start to distribute themselves in accordance with the concentration gradient in the volume of liquid formed by the extraction agent 12 on the deposition site 4. This can be seen on the left in FIG. 1D. The right side of FIG. 1D shows how a matrix solution 18 is deposited on the sample site 6 with a pipette 16. The matrix solution 18 contains a solvent and the dissolved matrix substance, which forms a crystal structure after the solvent has dried. The solvent of the matrix solution 18 and the extraction agent 12 can have the same composition or different compositions. No analyte molecules 14 are contained in the volume of liquid of the matrix solution 18 on the sample site 6 at this stage of the method.

In order to transfer analyte molecules 14 from the volume of liquid of the extraction agent 12 on the deposition site 4 to the sample site 6, a liquid communication is established between the two volumes of liquids across the sample support 2. This liquid communication is produced in the example shown in FIG. 1E by a liquid bridge 20 between the two volumes of liquid. A liquid bridge 20 can be produced, for example, by drawing the tip of a pipette from the volume of liquid on the sample site 6 to the volume of liquid on the deposition site 4, or vice versa, while releasing a liquid and thus drawing a trace of liquid on the sample support 2. This can be carried out manually or automated in the sense of an active operation.

The liquid bridge 20 does not necessarily require an additional volume of liquid. Instead, one of the liquids already present at the deposition site 4 and/or sample site 6 can be used—by executing a wiping movement—to produce the liquid bridge 20. These versions serve as—not all encompassing—examples for actively producing a liquid communication. The matrix solution 18, the extraction agent 12 or a combination of both can particularly be used to produce the liquid bridge 20.

Since no dissolved analyte molecules 14 are present in the volume of liquid on the sample site 6—for example proteins or peptides—some of the analyte molecules 14 in the volume of liquid on the deposition site 4 follow the concentration gradient across the liquid bridge 20. In this process, the concentration ratios of the individual dissolved molecular species which are present in the volume of liquid on the deposition site 4 are reproduced largely true to scale in the volume of liquid on the sample site 6. The insoluble cell residues which are left after the decomposition remain at the deposition site 4. As is illustrated, the volume of liquid of the liquid bridge 20 is small in comparison to the volumes of liquid of the extraction agent 12 on the deposition site 4 and the matrix solution 18 on the sample site 6 (especially if one takes into account the dimension of the liquid bridge perpendicular to the plane of projection, which is usually smaller than the dimension of a drop of liquid). In this way the probability can be minimized that, for example, individual fibers of the decomposed biological material of the analyte material 10 are transferred by means of diffusive and/or convective processes (like suspended particles) from the deposition site 4 across the liquid bridge 20 to the sample site 6, where their presence makes the matrix formation less homogeneous, at least on a small scale.

The liquid bridge 20 is preferably maintained until the concentration of the dissolved analyte molecules 14 in the communicating volumes of liquid has equalized. The liquid communication can then be stopped by drying (shown in FIG. 1F; black). The drying can be controlled by heating the region of the sample site 6 (not shown), by decreasing the vapor pressure conditions above the sample site 6 or a combination of both; in particular it can be accelerated after a predetermined timespan.

The method described with reference to FIG. 1 is also suitable for the preparation of biological material which has a high resistance to decomposition and on which the extraction agent has to act for a long period of time in order to release the components of interest from the cell interior, or on which a very strong extraction agent must be used. In contrast to the procedure which has been usual to date—according to which the biological material is deposited directly onto the sample site and decomposed there through the action of an extraction agent or solvent, after which the dissolved cell components are embedded into the forming crystal structure in a drying process—the process of decomposition and the process of embedding into the matrix crystal structure can be spatially separated from each other. Thus the drying of the matrix solution on the sample site no longer represents a time limit for the decomposition of the biological material. By overdosing or enhancing the decomposition capability of the extraction agent or solvent correspondingly, it is possible to wait until the biological material has been completely decomposed before the soluble components of the decomposed material are removed, in the form of the analyte molecules, among other things, and embedded into the forming matrix crystal structure on the sample site provided for the laser desorption.

Figure 2:
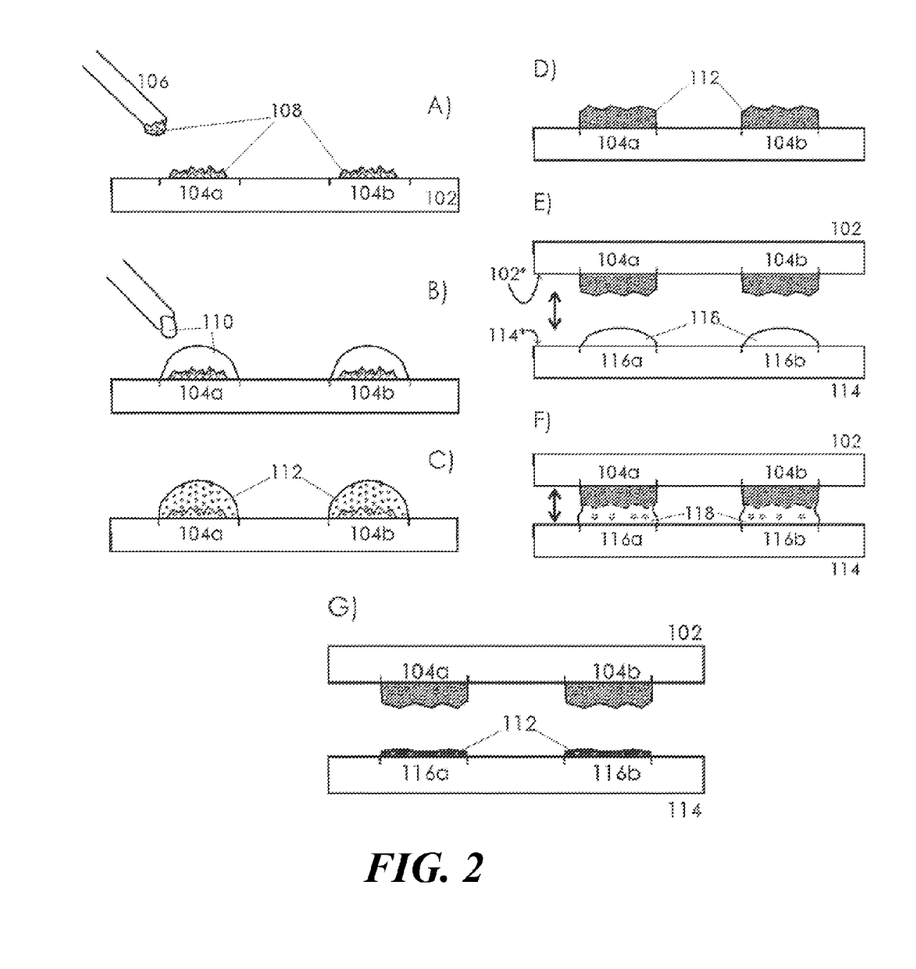

FIG. 2 shows a further example embodiment of a method for sample preparation. FIG. 2A shows how a support structure 102 with two deposition sites 104a, 104b is provided, and the two deposition sites 104a, 104b are coated with a biological material as the analyte material 108 with the aid of an inoculation swab 106. This can be automated or carried out manually. The biological material disposed on the two deposition sites 104a, 104b can be the same or can be different. The support structure 102 can be a portable plate, for example. As can be seen in FIG. 2B, an extraction agent is applied to the biological material in order to digest it. The decomposition releases the interesting components of the interior of the cell, such as proteins and/or peptides, as analyte molecules 112 (stars) and these disperse through the volumes of liquid on the deposition sites 104a, 104b (FIG. 2C).

In this example the volatile components of the extraction agent 110 are vaporized. The insoluble cell components or cell residues therefore remain on the deposition sites 104a, 104b and form a type of crust (gray) on the deposition sites 104a, 104b (FIG. 2D), together with the soluble components such as the analyte molecules of interest 112. A sample support 114 can be provided in parallel. The number and arrangement of sample sites 116a, 116b on this sample support 114 are preferably identical to the number and arrangement of the deposition sites 104a, 104b on the support structure 102. A matrix solution 118, containing molecules of the matrix substance in solution (not shown here) in addition to the solvent, is deposited onto the sample sites 116a, 116b of the sample support 114 by means of a pipette (not shown), for example. The support structure 102 and the sample support 114 are then positioned with the fronts 102*, 114* facing each other so that each deposition site 104a, 104b is opposite a sample site 116a, 116b (FIG. 2E). It is preferable to place the support structure 102 upside down, because gravity cannot cause the dried crust of the decomposed cell material to deform.

With a relative movement (double-headed arrow), the sample support 114 and the support structure 102 are brought closer together until the volumes of liquid on the sample sites 116a, 116b come into contact with the crust of dried cell components on the deposition sites 104a, 104b (FIG. 2F), and thereby a liquid communication is established. Particularly the solvent in the matrix solution 118 causes the crust to be partially dissolved in this process, and the soluble cell components in the dissolved portion disperse throughout the volumes of liquid on the sample sites 116a, 116b. The concentration ratios of the individual analyte molecules are reproduced largely true to scale because—as is shown in FIG. 2C—the soluble cell components can disperse freely in the volumes of liquid of the extraction agent 110 on the deposition sites 104a, 104b.

A further movement (double-headed arrow) of the sample support 114 and the support structure 102 relative to each other can stop the contact again after a certain time (FIG. 2G). Some analyte molecules 112 which were in the dissolved portion of the crust on the deposition sites 104a, 104b have transferred to the sample sites 116a, 116b, where they are embedded into the matrix crystal structure (black) which is formed in the subsequent drying process. The duration of contact required in order to ensure a largely complete equalization of the concentration of the analyte molecules 112 in the volumes of liquid on the sample sites 116a, 116b can be determined empirically, for example. The drying process can also be controlled according to this embodiment by means of targeted heating or by changing the vapor pressure conditions (not shown). It is thus possible to prepare a sample support 114 for ionization with matrix-assisted laser desorption with a largely homogeneous matrix crystal structure which is particularly suitable for laser desorption and which contains a sufficient number of analyte molecules 112 for the mass spectrometric analysis.

Figure 3:
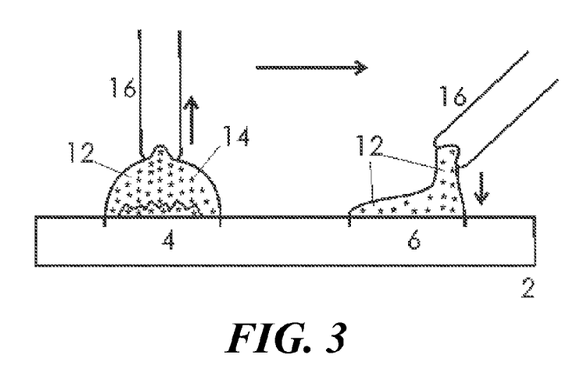

FIG. 3 illustrates an alternative step for the continuation of the preparation method depicted in the FIGS. 1A to 1C in accordance with the invention, which can be used instead of that shown in FIGS. 1D to 1F. Here a pipette 16 is used to take up a portion of the liquid supernatant of the extraction agent 12 which contains the dissolved analyte molecules 14 from the deposition site 4; the pipette is then moved to the separate sample site 6 (see arrows), where it releases the quantity of extraction agent 12 taken up. In this simple method, interference with the matrix crystallization is prevented by spatially separating the site where the analyte material is decomposed from the site where the matrix crystallizes. This is effective because the insoluble cell components or cell residues are only present in the liquid supernatant of the extraction agent 12 in negligible amounts and accordingly are not taken up by the pipette 16, or scarcely at all. Since the deposition site 4 and the sample site 6 are separate, yet in close proximity on the same sample support 2, the method shown in FIG. 3 is particularly suitable for manual sample preparation in the laboratory. Automated solutions with appropriate pipette positioning systems are also conceivable, however.

Figure 4A:
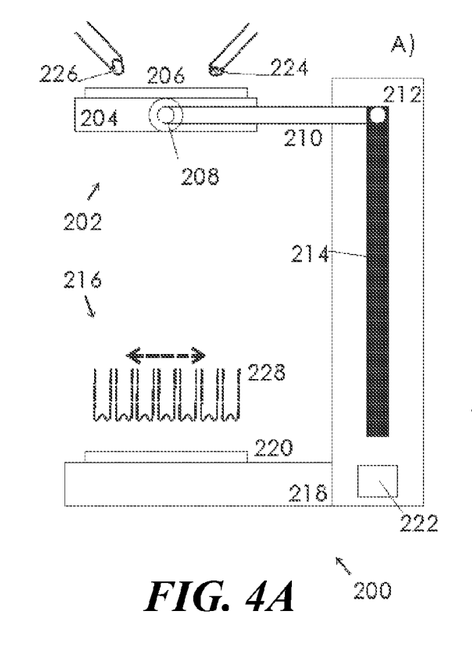
Figure 4B:
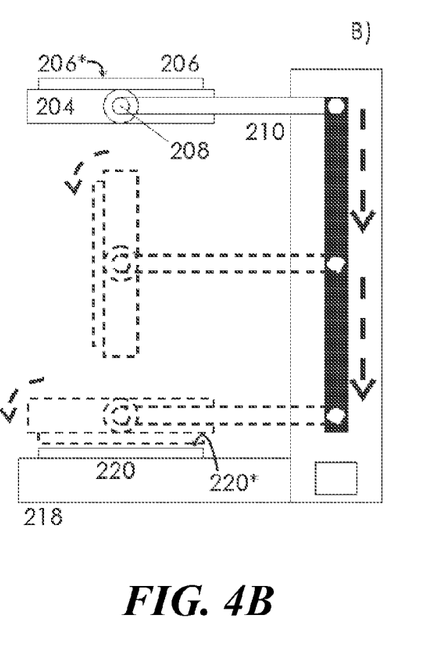

FIGS. 4A and 4B show an example embodiment for a device 200 for sample preparation for ionization with matrix-assisted laser desorption. The device 200, as shown in FIG. 4A, has a deposition unit 202, which is here equipped with a support plate 204 as the holder. A support structure 206 can be positioned and fixed on the support plate 204. The support structure 206 can be clamped to the support plate 204, for example. The support plate 204 rests on a pivot 208 located in the center of the support plate 204 so that the support plate 204 can rotate. The pivot 208 is connected to a support column 212 via an arm 210. The end of the arm at the support column 212 is in operative connection with an actuator which can execute a linear movement in a slot 214 located on the support column 212. In the example shown, the pivot 208 and the linear actuator form the positioning device of the device 200. The height of the arm 210 with the support plate 204 and, if required, with the support structure 206 located on the support plate 204 can be adjusted by means of the actuator.

The device also has a sample unit 216, which is located at the lower end of the support column 212 in the form of a base plate 218. The base plate 218 comprises a holder for a sample support 220, on the one hand, and contributes to the stabilization of the device 200, comprising the deposition unit 202, sample unit 216 and the positioning device, on the other hand. The control system 222, which communicates at least with the components of the positioning device—i.e. with the pivot 208 and the actuator in the example shown—is also located on the support column 212. It can operate the components of the positioning device by transmitting control signals and detect their movement status by receiving feedback signals. The control system 222 can have an appropriately programmed microprocessor, for example.

In one embodiment, an analyte material 224 or quantities of liquid, for example an extraction agent or solvent 226, can be manually deposited on a support structure 206 which is located on the support plate 204. It is also possible to deposit a matrix solution manually on sample sites of a sample support 220 located on the base plate 218. It is preferable in this case to move the support plate 204 as far as possible from the base plate 218 by means of the actuator. Alternatively, there can also be pipetting devices for the automated deposition of liquid onto support structure 206 or sample support 220 located in the holders. In FIG. 4A, such a pipetting device is indicated by a row of pipette tips 228, which are suitable for simultaneous multiple liquid deposition on several sample sites. This makes it possible to accelerate the deposition of a matrix solution onto the sample sites, for example. The row of pipettes 228 can be positioned over a sample support 220 located on the base plate 218 and can be moved to the side after the liquid has been deposited (see broken, double-headed arrow). Such automated operation is preferably also coordinated by the control system 222, with which the pipetting devices can communicate for this purpose. A separate control of the pipetting devices is also conceivable, however.

With reference to the FIGS. 2E and 2F, FIG. 4B shows an example mode of operation which is used to bring the support structure 206 and the sample support 220 together. To this end, the actuator moves the arm 210 vertically (broken arrows) toward the base plate 218 and the sample support 220 located thereon. At the same time the support plate 204 with the support structure 206 fixed to it is rotated through 180° by means of the pivot 208 so that the front 206* of the support structure 206 and the front 220* of the sample support 220 are facing each other. It is also possible to carry out the linear movement and the rotational movement separately from each other. The important thing is that the rotation through 180° is finished before the fronts 206*, 220* are moved together to a contact distance, which is preferably defined by the establishment of a liquid communication. The last part of the bringing together is then preferably done via a precise linear movement of the actuator. The bringing together can be assisted by sensors (not shown) located on the base plate 218 and/or the support plate 204. In one version, the sensors can detect the approach of the support structure 206 and the sample support 220. Ultrasonic sensors or optical sensors (such as those emitting infrared light) can be used as proximity sensors, for example. In another version, the sensors can also monitor the establishment of the liquid communication between the sample sites on the sample support 220 and the deposition sites on the support structure 206. Capacitance or resistance sensors can be used for this purpose, for example.

Once the liquid communication has been established, for which no direct contact between the surfaces 206* and 220* is required but only sufficient proximity, and enough time for the transfer of the soluble cell components of the analyte material into the drops of matrix solution on the sample sites has elapsed, the liquid communication can be stopped by the actuator-controlled lifting of the support plate 204 away from the base plate 218. If required, the positioning cycle explained with the aid of FIG. 4B can be performed in reverse. The matrix solution residue which was enriched with the analyte molecules during the liquid communication and which has remained on the sample sites can now be vaporized. The sample on the sample site is in principle then ready for the laser desorption.

Figure 5:
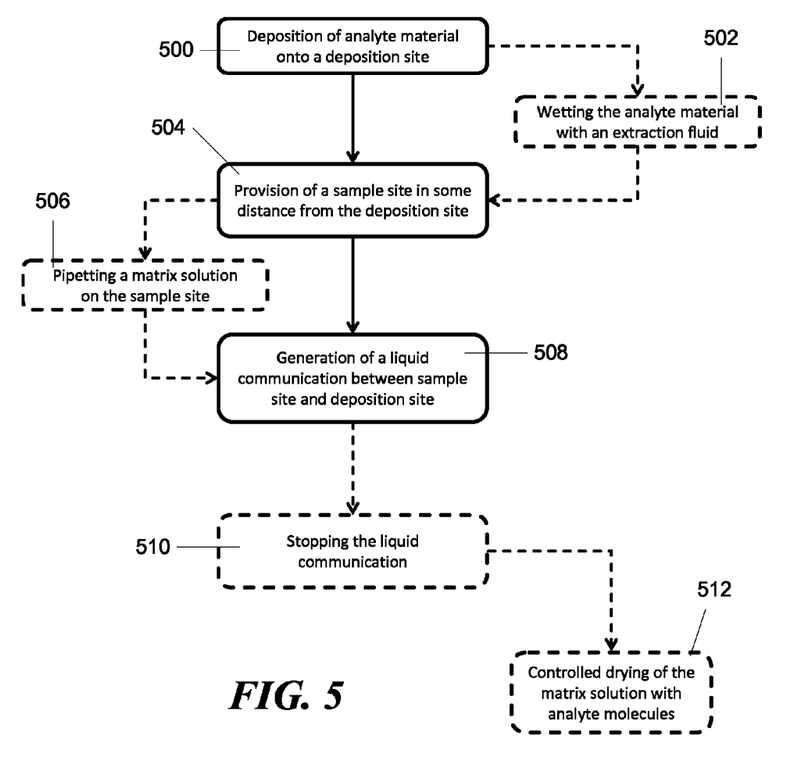

FIG. 5 shows a flow diagram of an embodiment of a method according to the invention. First, in step 500, an analyte material is deposited onto a deposition site. Then, in step 504, a sample site is provided which is at a distance from the deposition site and is intended as a support for a matrix. In one embodiment, a matrix solution can be deposited on the sample site. Then, in step 508, a liquid communication is established between the deposition site and the sample site. The liquid communication can consist of a liquid bridge. In a further embodiment, in step 502, the analyte material on the deposition site can be wetted with an extraction agent before the liquid communication is established, which brings about at least a partial decomposition. In a further embodiment, the liquid communication can be stopped (step 510) by drying the matrix solution, the extraction agent or a combination of the two. In a further embodiment, the drying can be controlled by heating the region of the sample site as set forth in step 512, by changing the vapor pressure conditions above the sample site or a combination of both.

Figure 6:
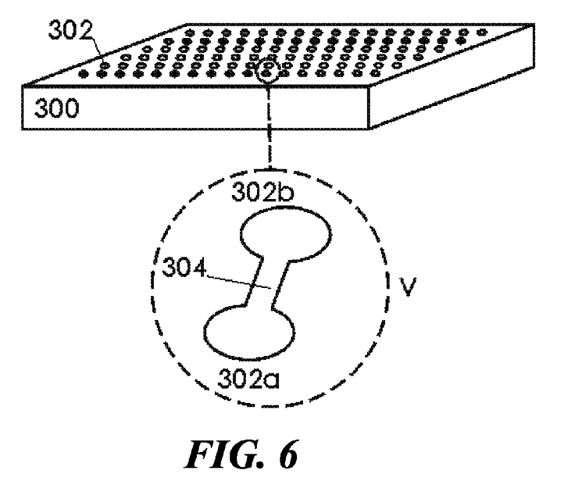

FIG. 6 is a schematic representation of an example embodiment of a sample support 300 with several sites 302 (on an essentially plane support surface), which can each act as deposition site or sample site. The sites 302 are characterized by the fact that they have hydrophilic properties, unlike the remaining surface of the sample support 300, which is hydrophobic. These properties enable the sites to localize and bind aqueous liquids, in particular. The enlarged section V shows two adjacent hydrophilic sites 302a, 302b on the surface of the sample support 300 which are connected with each other by a hydrophilic bridge 304. This illustration is not true to scale, and is only intended to illustrate the principle. If a drop of a liquid (not shown), for example a solvent or extraction agent, is deposited onto one of the sites, it can distribute across the whole hydrophilic area of the site 302a or 302b and can also spread into the region of the hydrophilic bridge 304, from where it can also reach the other site, a distance away. A liquid communication can thus be established very easily between the separate sites 302a and 302b, and it is only necessary to deposit a liquid on one of the sites 302a and 302b. In practice it may prove useful, in addition, to assist the liquid communication by adding a further quantity of liquid, such as by drawing a trace of liquid from one site 302a to the other 302b using a pipette. The section V shows a simple connection in the form of a narrow bridge between two sites 302a and 302b. It is also possible to connect a selected site 302a or 302b with several other sites via a hydrophilic bridge 304. Such a multiple connection can comprise a star-shaped connection to the immediately adjacent selected sites, for example. Furthermore, it is possible to provide some selected sites with a larger area than others (not shown). These can then preferably serve as deposition sites if a large quantity of an extraction agent or solvent is required to decompose cells of a microorganism.

It will be understood that various aspects or details of the invention may be changed, or that different aspects disclosed in conjunction with different embodiments of the invention may be readily combined if practicable, without departing from the scope of the invention. Furthermore, the foregoing description is for the purpose of illustration only, and not for the purpose of limiting the invention, which is defined solely by the appended claims.

What is claimed is:

1. A method for the preparation of samples for ionization with matrix-assisted laser desorption, comprising:
    (a) depositing an analyte material containing soluble analyte molecules of interest and in-soluble components onto a deposition site;
    (b) providing a sample site which is a distance away from the deposition site and is intended as a substrate for a matrix crystal layer;
    (c) establishing a liquid communication between the deposition site and the sample site, thereby promoting a transfer of soluble analyte molecules of interest from the deposition site to the sample site as a result of ever-present molecular processes in liquids and without exerting additional driving forces on the soluble analyte molecules for transferring them from the deposition site to the sample site while generally impeding the insoluble components from being transferred from the deposition site to the sample site; and
    (d) discontinuing the liquid communication after a predetermined time period.

2. The method according to claim 1, in which a matrix solution is deposited onto the sample site.

3. The method according to claim 1, in which, before step (c), the analyte material on the deposition site is wetted with an extraction agent, which brings about at least a partial decomposition of the analyte material for generally releasing the soluble analyte molecules of interest.

4. The method according to claim 3, in which the ratio of a quantity of the analyte material to one of a quantity and strength of the extraction agent is such that the analyte material is almost completely decomposed.

5. The method according to claim 1, wherein step (c) comprises producing a liquid bridge between the deposition site and the sample site.

6. The method according to claim 1, wherein step (d) comprises discontinuing the liquid communication by drying through at least one of heating and ventilating.

7. The method according to claim 1, in which the deposition site and the sample site are provided on physically separated support structures.

8. The method according to claim 7, in which the liquid communication is established in step (c) and discontinued in step (d) by a movement of the two support structures relative to each other.

9. The method according to claim 1, in which the analyte material contains at least one of microorganisms in untreated form and lysed microorganisms.

10. The method according to claim 1, in which the liquid communication is maintained until the concentration of the soluble analyte molecules has been approximately equalized at the deposition and the sample sites.

11. The method according to claim 1, in which the analyte material is deposited onto the deposition site in a solution containing a matrix substance.

12. The method according to claim 1, wherein a volume of liquid involved in the liquid communication is chosen such as to ensure that there is no diffusive or convective transfer of insoluble components from the deposition site to the sample site.

13. A method for the preparation of samples for ionization with matrix-assisted laser desorption, comprising:
    (a) depositing an analyte material containing soluble analyte molecules of interest and in-soluble components onto a deposition site;
    (b) providing a sample site which is a distance away from the deposition site and is intended as a substrate for a matrix crystal layer;
    (c) establishing a liquid communication between the deposition site and the sample site, thereby promoting a transfer of soluble analyte molecules of interest from the deposition site to the sample site as a result of diffusion due to a concentration gradient in a communicating volume of liquid and without exerting additional driving forces on the soluble analyte molecules for transferring them from the deposition site to the sample site while generally impeding the insoluble components from being transferred from the deposition site to the sample site; and
    (d) discontinuing the liquid communication after a predetermined time period.

* * * * *